US00PP16289P3

(12) United States Plant Patent
Roose et al.

(10) Patent No.: US PP16,289 P3
(45) Date of Patent: Feb. 28, 2006

(54) MANDARIN HYBRID TREE NAMED 'TDE4'

(50) Latin Name: *Citrus reticulata*
Varietal Denomination: TDE4

(75) Inventors: Mikeal L. Roose, Riverside, CA (US); Timothy A. Williams, Riverside, CA (US); Robert K. Soost, Inverness, CA (US); James W. Cameron, Salem, OR (US)

(73) Assignee: The Regents of the University of California, Oakland, CA (US)

( * ) Notice: Subject to any disclaimer, the term of this patent is extended or adjusted under 35 U.S.C. 154(b) by 224 days.

(21) Appl. No.: 10/177,417

(22) Filed: Jun. 20, 2002

(65) Prior Publication Data

US 2003/0237120 P1 Dec. 25, 2003

(51) Int. Cl.
*A01H 5/00* (2006.01)

(52) U.S. Cl. ..... Plt./202

(58) Field of Classification Search ..... Plt./202, Plt./201

See application file for complete search history.

*Primary Examiner*—Kent Bell
(74) *Attorney, Agent, or Firm*—Townsend and Townsend and Crew LLP

(57) ABSTRACT

A new mandarin hybrid called "TDE4" is distinguished by production of fruit that combine mid-late season maturity, large fruit size, attractive deep orange rind color and virtual absence of seeds with rich fruit flavor.

7 Drawing Sheets

Genus and species:
This application is directed to a description of TDE4, which is a mandarin orange tree (*Citrus reticulata*).

BACKGROUND OF THE INVENTION

The pedigree of TDE4 is shown in FIG. 1. In 1973, pollen from Encore mandarin (unpatented to Applicant's knowledge) was applied to stigmas of a tetraploid (Temple× 4N Dancy) hybrid (unpatented to Applicants' knowledge) and the pollinated flowers were bagged to prevent insect pollination. Fruits were collected in winter 1974, seeds extracted from each fruit, and each seed was planted. The chromosome number of each seedling was determined and those identified as triploid seedlings were budded onto Troyer rootstock. The resulting trees were planted in the field in Riverside, Calif. in 1976. These trees were evaluated for tree vigor, bearing, and seediness, fruit flavor, fruit color, and other fruit quality traits from bearing until 1985. Five trees were selected from the original population and repropagated by budding onto C-32 citrange, C-35 citrange, Troyer citrange, and trifoliate orange rootstocks. Two trees of the selection now called TDE4 were planted in the field in Riverside in 1987. When they began fruiting (approximately in 1990), these trees were evaluated for the same tree and fruit quality traits as the original trees. In 1987, the selection now called TDE4 was chosen for additional testing because it combined medium or large fruit size, low seed number, rich fruit flavor, deep orange rind and flesh color, and acceptable peelability. Budwood of this selection was tested for viruses and other pathogens by the Citrus Clonal Protection Program and virus-free bud source trees were planted in Lindcove Research and Extension Center, Exeter, Calif. in 1991.

Using this virus-free budwood source, additional trees were propagated and planted at several California locations between 1993 and 1996. These included one location in the Coachella Valley (the Coachella Valley Agricultural Research Station-CVARS, 8 trees), Ojai (12 trees ) and Santa Paula (5 trees) in Ventura Co., and two locations in the San Joaquin Valley, (Lindcove Research and Extension Center, 8 trees, and Orange Cove, 8 trees). These trial plantings provide most of the available data on TDE4. Several different rootstocks have been used in these evaluations, including Carrizo citrange, C35 citrange, Rich 16-6 trifoliate, Cleopatra mandarin, and Schaub rough lemon. In general, no major effects of these rootstocks on fruit quality of TDE4 were observed, and no incompatiblities have been evident, but longevity of trees on various rootstocks is not known. Effects of rootstocks on tree size are discussed below.

ASEXUAL REPRODUCTION

The plant known as TDE4 was first asexually propagated in 1975 when buds were collected from hybrid seedling 73-45-5 and grafted onto Troyer citrange rootstock in a greenhouse in at the University of California, Riverside, Calif., U.S.A. This tree was grown in a greenhouse and in 1976 it was planted in Field 6D, Row 11, Tree 21 at the Citrus Research Center, University of California, Riverside, Calif., U.S.A. Additional asexual propagation took place in 1986 when buds were collected from field tree 6D-11,21 and grafted onto 'C32' citrange and trifoliate orange rootstocks. All characteristics of the original tree, and its fruit, were established and appear to be transmitted through succeeding asexual propagations.

BRIEF SUMMARY OF THE INVENTION

The present invention provides a novel mandarin hybrid having the characteristics described and illustrated herein. The hybrid TDE4 produces fruit that combine mid-late season maturity, large fruit size, attractive deep orange rind color and virtual absence of seeds with rich fruit flavor.

BRIEF DESCRIPTION OF THE DRAWINGS

FIG. 4 illustrates the solids:acid ratio of TDE4 at Santa Paula, Calif. over five years. Points plotted are means of all samples collected on a given date. Solid lines connect means for sampling dates within the same season. The dashed line is a liner regression of solids:acid on sampling date using data from all years. The regression equation and $r^2$ value are shown.

FIG. 5 illustrates the solids:acid ratio of TDE4 at Lindcove, Calif. over five years. Points plotted are means of all samples collected on a given date. Solid lines connect means for sampling dates within the same season. The dashed line is a liner regression of solids:acid on sampling date using data from all years. The regression equation and $r^2$ value are shown.

FIG. 6 illustrates the solids:acid ratio of TDE4 at Orange Cove, Calif. over five years. Points plotted are means of all samples collected on a given date. Solid lines connect means for sampling dates within the same season. The dashed line is a liner regression of solids:acid on sampling date using data from all years. The regression equation and $r^2$ value are shown.

FIG. 7 illustrates the solids:acid ratio of TDE4 at Ojai, Calif. over five years. Points plotted are means of all samples collected on a given date. Solid lines connect means for sampling dates within the same season. The dashed line is a liner regression of solids:acid on sampling date using data from all years. The regression equation and $r^2$ value are shown.

DETAILED DESCRIPTION OF THE INVENTION

All major color code designation are by reference to The R.H.S. Colour Chart (2001) provided by The Royal Horticultural Society of Great Britain.

Eight to ten year-old trees grown in the ground were examined to prepare the description in this and the following paragraph. Tree shape (FIG. 2) is approximately sphereoid, rather similar to that of orange trees. The trees have not been noted as particularly susceptible to any diseases and, based on a freeze in 1999, appeared only slightly more cold hardy than oranges of similar age. Leaves (FIG. 2) are simple, brevipetiolate, lanceolate, with entire or slightly margins. The petiole shape is narrow and linear in shape. In comparison with most old-line *citrus* cultivars, trees of TDE4 are somewhat thorny, with normal branches having short length (4 mm) thorns at about 13% of the nodes, and vigorous sprouts having short (3 mm) thorns at about 3% nodes. Thorniness will probably decrease as the cultivar ages.

Figure 1:
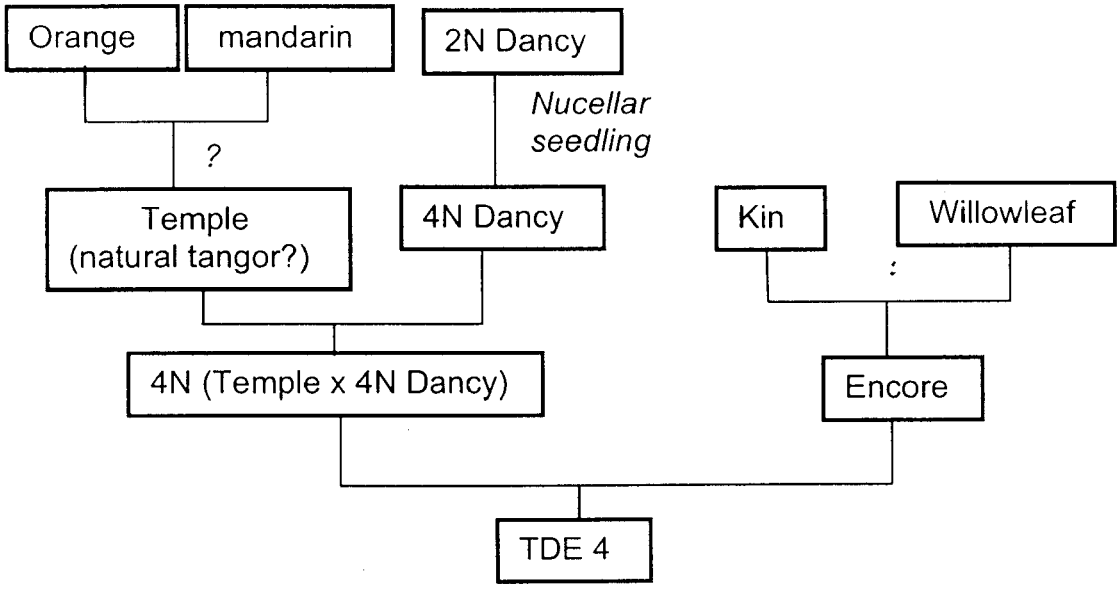
FIG. 1 illustrates the pedigree of TDE4. All cultivars are *C. reticulata* except orange, which is *C. sinensis*.
Figure 2:
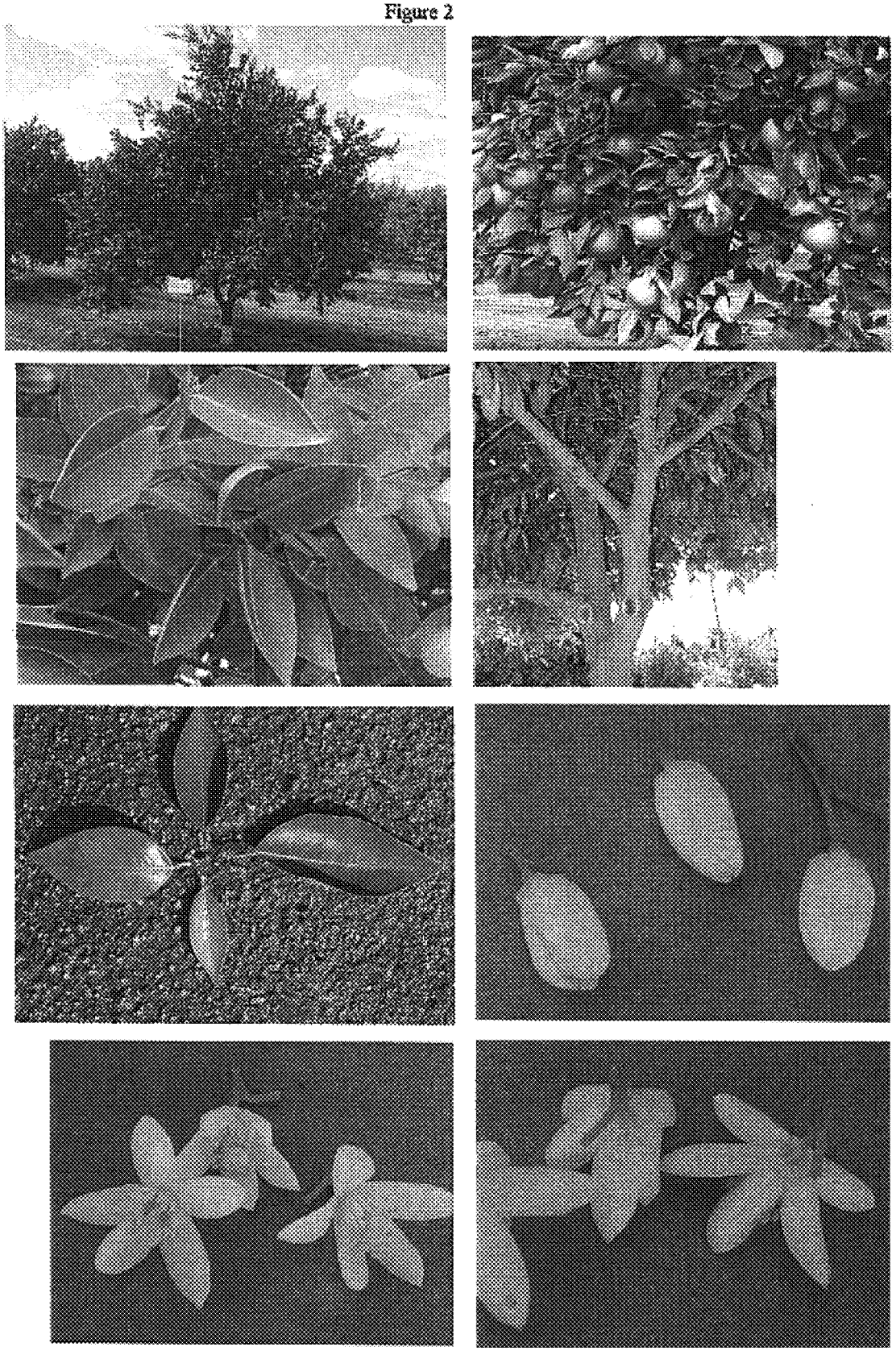
FIG. 2 illustrates, clockwise from top left: a nine-year-old tree of TDE4 on Carrizo rootstock; fruit on tree; branching pattern; flower buds; leaves; and shoots.

Flowers of TDE4 are typically hermaphroditic, with Green-White 157D petals and yellow 13B anthers (FIG. 2). Trees flower from early April into May at most locations. Pollen is somewhat sparse, with viability (estimated in an in vitro germination test) of 8%. Pollen tube growth is also less than that of fertile, diploid mandarins.

The height and spread of a mature (27 years old) TDE4 tree is as follows: Tree height=6.0 m; Width=6.25 m. Trunk diameter of a 27 year old tree was 25.6 cm when measured 38 cm above the ground. Trunk color using the R.H.S. Colour Chart is Brown N200B.

Leaf characteristics of TDE4 trees are as follows:

*Leaf shape.*—Ovate.

*Blade length.*—83.6 mm.

*Blade width.*—44.7 mm.

*Apex description.*—Acute with weak emargination.

*Base description.*—Convex.

*Abaxial leaf color* (*RHS chart*).—Yellow Green 146B.

*Adaxial leaf color* (*RHS chart*).—Yellow Green 147A.

Petiole characteristics of TDE4 trees are as follows:

*Petiole length.*—11.8 mm.

*Petiole width.*—2.0 mm.

*Petiole color* (*RHS chart*).—Yellow Green 147A.

If sufficient fruit was available, 10-fruit samples were collected from each location two or three times each year beginning in 1997 or 1998. Generally samples were collected from two or three trees per location on each sampling date. These fruit were evaluated in Riverside for a range of traits as summarized in Table 1.

TABLE 1

Fruit characteristics of TDE4 averaged over 4 locations and 4 seasons. Samples were collected from mid-January to early May at Santa Paula, Ojai, and Lindcove, and from mid-January to mid-March at Orange Cove. "N" indicates the total number of fruit samples analyzed. Results are averaged over several rootstocks. The trees examined for Table 1 ranged from 3–8 years old and were grown in the ground.

| Trait | N | Min | Max | Mean | SD |
|---|---|---|---|---|---|
| Fruit height (mm) | 201 | 47.5 | 76.8 | 58.3 | 5.29 |
| Fruit width (mm) | 201 | 59.6 | 102.1 | 74.7 | 7.15 |
| Fruit height:width | 201 | 0.67 | 0.91 | 0.78 | 0.045 |
| Rind color | 201 | 4.5 | 13.0 | 12.3 | 1.04 |
| Rind texture | 201 | 2.3 | 5.0 | 3.3 | 0.57 |
| Neck | 201 | 0 | 2.00 | 0.23 | 0.430 |
| Peelability | 201 | 5.00 | 10.00 | 8.23 | 0.850 |
| Rind thickness (mm) | 201 | 3.00 | 6.00 | 4.21 | 0.687 |
| Seeds per fruit | 201 | 0 | 5.00 | 0.32 | 0.696 |
| Fruit weight (g) | 201 | 91.0 | 335.0 | 174.5 | 41.94 |
| Juice content (%) | 195 | 18.2 | 56.3 | 42.2 | 6.91 |
| Soluble solids (%) | 195 | 7.85 | 19.50 | 12.31 | 1.698 |
| Acid (%) | 195 | 0.56 | 2.03 | 1.13 | 0.302 |
| Solids:acid | 195 | 5.81 | 24.60 | 11.61 | 3.332 |

[a]Visual rating on a scale of 0–13; 0 = green, 13 = red-orange

[b]Visual rating on a scale of 1–8; 1 = very smooth, 8 = extremely coarse

[c]Visual rating on a scale of 0–3; 0 = no trace of neck, 3 = neck with a diameter at least 50% of fruit diameter

[d]Subjective rating of ease of peeling a single fruit; 1 = very difficult, 10 = a fruit with completely separated rind and segments. Fruit with ratings of 7 or higher would be relatively easy to peel.

Figure 3:
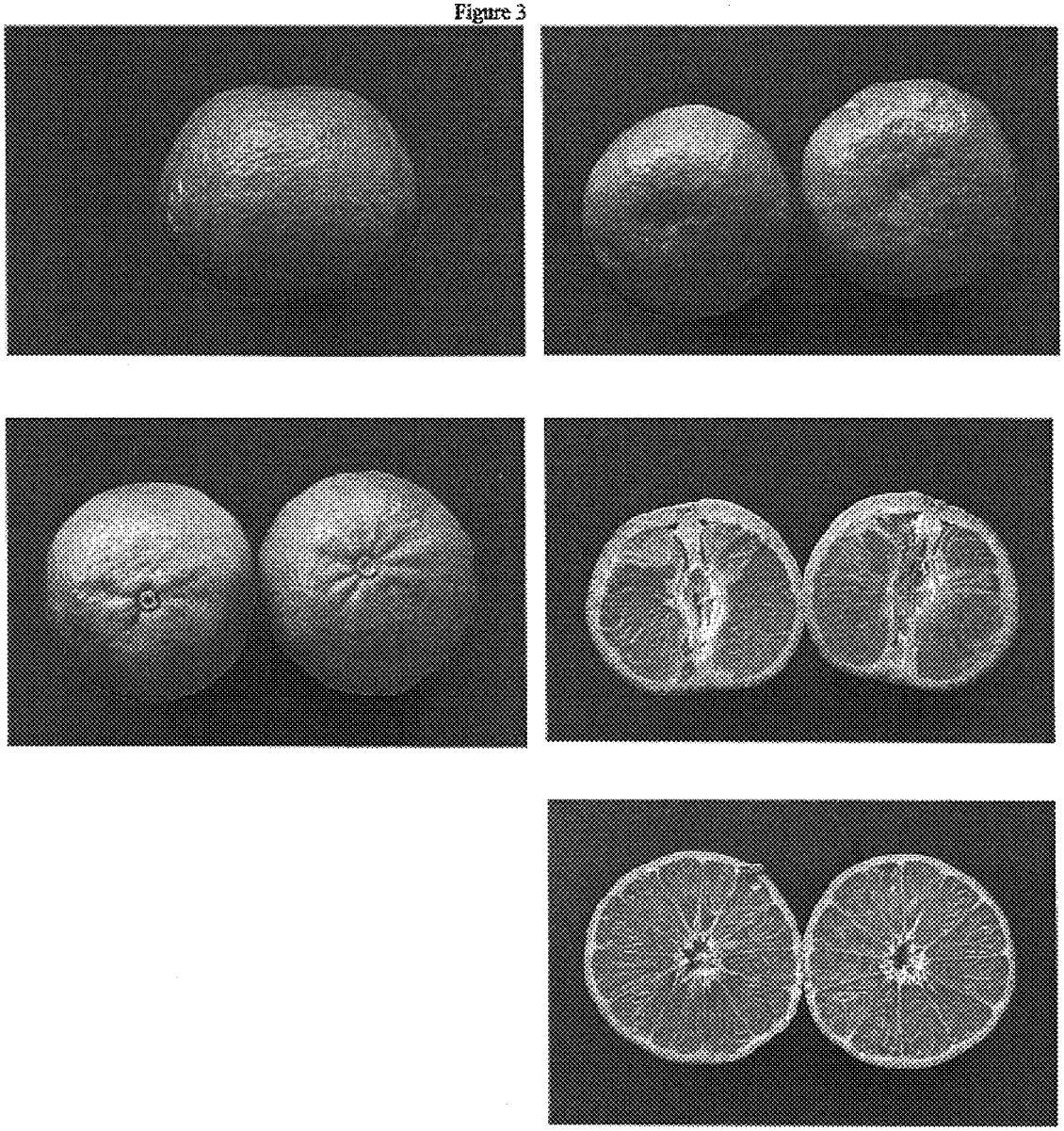
FIG. 3 illustrates fruit of TDE4 sampled from nine-year-old tree on Carrizo rootstock.

Based on this data, TDE4 fruit are oblate in shape (FIG. 3), with little or no neck. The average fruit size is large for a mandarin (classed as Mammoth by California state standards). Rind color is orange-red N30C. The rind texture is somewhat variable, depending on tree age and crop. For older trees with a moderate to heavy crop, rind texture is smooth, with conspicuous oil glands (about 50 $cm^2$). The rind of fruit from trees with very light crops is sometimes excessively rough or bumpy. The rind is quite easy to peel when fruit are mature, but can be more adherent early in the season. Fruit flesh color is orange 28A. Flesh thickness is about 68 mm. Albedo color is Yellow-White 158B. Albedo thickness is about 2.0 mm. Adherence of rind to pulp is medium or moderate. The number of segments per fruit is 9–10. The fruit base (stalk end) is slightly concave (FIG. 3), and the apex is truncate with a slight depression in the stylar end and a small (2 mm), usually closed, stylar scar.

Important determinants of maturity date for *citrus* fruit are the solids:acid ratio and juice content. Using data for all years, juice content show a statistically significant correlation with sampling date at only at Santa Paula, where the slope of the regression was positive. Regressions were slightly negative at the other three locations, but not significantly so. This indicates that at Santa Paula, the site with the latest maturity date, fruit sampled from mid-January to mid-February had not yet reached maturity. At the other locations, juice content showed little tendency to decrease later in the season. Solids:acids ratio was significantly correlated with sampling date at all location except Santa Paula (FIG. 4). Using these regressions, the estimated dates on which fruit reached an 8:1 solids:acid ratio was January 2 for Ojai, January 15 for Orange Cove, January 16 for Lindcove, and January 27 for Santa Paula.

During the 1999–2000 season, fruit of TDE4 and several other mandarin varieties were harvested, run over a packline at the University of California Lindcove Research and Extension Center, waxed and evaluated by a taste panel. Evaluations were done before storage, after storage for 11 days at 68 F, and after storage for 21 days at 37 F. Fruit were rated on a 9 point scale, where a score of 1 is "Dislike extremely", 5 is "Neither dislike or like", and 9 is "Like extremely". Fruit were sampled from test plots at Lindcove and Orange Cove on February 23 (Table 2) and Mar. 21, 2000 (Table 3). These samples would represent mid-late season fruit of TDE4, the fruit from Lindcove and Orange Cove having solids:acid ratios of 10.8 and 10.5 on February 18 and 15.1 and 14.3 on March 14 respectively. TDE4 fruit from the two locations were similar in all traits evaluated. Their ratings were good for all traits before storage, and were little changed by storage at room temperature or at 37 F. TDE4 had higher scores than Gold Nugget and W. Murcott for visual appeal and similar peelability. It also had slightly higher taste scores in most comparisons.

TABLE 2

Sensory panel evaluation of TDE4 (TDE4L), Gold Nugget, W. Murcott from Lindcove and TDE4 from Orange Cove (TDE4M) harvested February 22, 2000.

| Storage | | TDE4L | TDE4M | Gold Nugget | W. Murcott |
|---|---|---|---|---|---|
| | | Visual Evaluation | | | |
| Initial | Mean | 7.0 | 7.2 | 3.6 | 5.3 |
| | SD | 1.6 | 1.4 | 1.6 | 1.6 |
| 11 days | Mean | 7.2 | 7.3 | 6.7 | 5.3 |
| @ 68 F | SD | 1.1 | 1.3 | 1.2 | 2.0 |
| 21 days | Mean | 7.2 | 7.5 | 6.7 | 4.2 |
| @ 37 F | SD | 1.6 | 1.7 | 2.2 | 1.8 |
| | | Peelability Evaluation | | | |
| Initial | Mean | 7.5 | 6.8 | 7.2 | 6.6 |
| | SD | 0.8 | 2.2 | 1.5 | 2.1 |
| 11 days | Mean | 6.7 | 7.2 | 8.1 | 7.5 |
| @ 68 F | SD | 1.6 | 1.7 | 1.3 | 1.7 |
| 21 days | Mean | 7.1 | 7.6 | 8.0 | 7.0 |
| @ 37 F | SD | 1.7 | 1.9 | 1.8 | 2.0 |
| | | Taste Evaluation | | | |
| Initial | Mean | 7.3 | 7.2 | 6.5 | 6.2 |
| | SD | 1.1 | 1.7 | 1.6 | 1.9 |
| 11 days | Mean | 6.1 | 5.9 | 5.5 | 6.9 |
| @ 68 F | SD | 2.5 | 1.9 | 2.1 | 2.5 |
| 21 days | Mean | 6.7 | 6.6 | 5.7 | 6.9 |
| @ 37 F | SD | 2.1 | 1.9 | 1.9 | 2.1 |

TABLE 3

Sensory panel evaluation of TDE4 (TDE4L), Gold Nugget, W. Murcott from Lindcove and TDE4 from Orange Cove (TDE4M) harvested March 20, 2000.

| Storage | | TDE4L | TDE4M | Gold Nugget | W. Murcott |
|---|---|---|---|---|---|
| | | Visual Evaluation | | | |
| Initial | Mean | 6.8 | 7.1 | 4.5 | 6.6 |
| | SD | 1.6 | 1.7 | 1.3 | 1.4 |
| 11 days | Mean | 6.9 | 7.4 | 5.8 | 7.3 |
| @ 68 F | SD | 1.5 | 1.5 | 1.2 | 0.9 |
| 21 days | Mean | 6.8 | 7.5 | 6.9 | 5.3 |
| @ 37 F | SD | 2.1 | 1.1 | 1.4 | 2.2 |
| | | Peelability Evaluation | | | |
| Initial | Mean | 6.9 | 7.2 | 7.7 | 7.8 |
| | SD | 1.8 | 1.9 | 1.0 | 0.9 |
| 11 days | Mean | 6.6 | 7.3 | 7.6 | 7.6 |
| @ 68 F | SD | 1.6 | 1.4 | 1.5 | 1.3 |
| 21 days | Mean | 7.0 | 7.7 | 7.8 | 7.1 |
| @ 37 F | SD | 1.6 | 1.2 | 1.4 | 1.8 |
| | | Taste Evaluation | | | |
| Initial | Mean | 7.5 | 6.9 | 7.1 | 6.8 |
| | SD | 1.2 | 1.4 | 1.7 | 1.9 |
| 11 days | Mean | 7.0 | 6.8 | 6.7 | 6.7 |
| @ 68 F | SD | 2.1 | 1.3 | 1.8 | 1.7 |
| 21 days | Mean | 7.4 | 6.7 | 6.3 | 6.6 |
| @ 37 F | SD | 1.8 | 1.4 | 1.8 | 1.7 |

Yield of TDE4 was evaluated from visual ratings of crop relative to tree size at each location from 1998–99 to 2001–2002. The rating scale ranged from 0 (no crop) to 5 (very heavy crop). Crops at Ojai were fairly good, being 2–3.3 during the last three of the four years evaluated. At Santa Paula, crop ratings indicated moderate alternate bearing, with average values of 0.50, 2.60, 0.88, and 2.90 from 1998–99 to 2001–2002 respectively. Trees planted at Lindcove in 1994 showed similar behavior, 2.94, 1.88, 1.50, and 2.90 from 1998–99 to 2001–2002 respectively. At Orange Cover, trees showed rather severe alternate bearing with crop ratings of 1.88, 4.00, 0.06, and 1.60. Yield at Lindcove in 2000 and 2001 was 29 and 14 kg tree, while at Orange Cove it was 66 and 0 kg tree. Trees appear to flower profusely, but fruit set is virtually absent.

Trees that were screened to exclude bees during flowering produced very few fruit for two consecutive years, but it is possible that TDE4 is self-fertile but requires pollination for fruit set. As discussed above, tree fruit is set in April and May. First and last harvest dates for Riverside California are estimated as February 15 and May 15. Because TDE4 is a mid-late season fruit, it is likely that trees will show a fairly strong tendency to alternate bearing, and this is supported by the data for some locations.

Two siblings of TDE4, "TDE2" and "TDE3," were compared to TDE2. TDE4 is distinct from these cultivars in having a smoother rind, intermediate maturity date, and distinctive flavor. TDE4 fruit are more oblate in shape than those of TDE3, and the rind color of TDE4 is deeper orange than that of TDE2. Trees or fruit of TDE4 can be distinguished from those of other mandarins, including TDE2 and TDE3, using simple sequence repeat (SSR) DNA markers. Using TDE4 DNA as template, PCR primer set TAA3 (F=AGAGAAGAAACATTTGCGGAGC (SEQ ID NO:1), R=GAGATGGGACTTGGTTCATCACG (SEQ ID NO:2)) amplified a band of 145 bp while TDE2 and TDE3 had both had two bands of 142 and 145 bp. Primer sets TAA3 plus CAC15 (F=TAAATCTCCACTCTGCAAAAGC (SEQ ID NO:3), R=GATAGGAAGCGTCGTAGACCC (SEQ ID NO:4)) and TAA15 (F=GAAAGGGTTACTTGACCAGGC (SEQ ID NO:5), R=CTTCCCAGCTGCACAAGC (SEQ ID NO:6)) distinguished TDE4 from the following cultivars: Dancy, Encore, King, Willowleaf, Wilking, Gold Nugget, Pixie, W. Murcott, Ellendale, Hernandina Clementine, Fortune, Kara, Kinnow, Murcott, Nova, and Ponkan.

The seed parent of TDE4 is a tetraploid hybrid between a 'Temple' tangor and a tetraploid tree of 'Dancy' mandarin. The tetraploid (Temple×4N Dancy) parent (referred to below as 4N-TD) was never released by the University of California and only two trees of this variety exist. TDE4 is distinct from this variety in having less than 1 seed per fruit while 4N-TD averages 10 seeds per fruit. Fruit of 4N-TD have an aspect ratio of about 0.88, mature in December–January and hold on the tree for about 1 month, while those of TDE4 have an aspect ratio of about 0.78, mature in February and hold on the tree for 2–3 months. Fruit of 4N-TD have thicker rinds (5.5 mm) than those of TDE4. Trees of 4N-TD are somewhat smaller (3.8 m tall) than those of TDE4 (5.9 m tall).

The pollen parent of TDE4 is 'Encore' mandarin. TDE4 differs from Encore in that Encore fruit average about 20 seeds per fruit while fruit of TDE4 have less than 1 seed per fruit. Encore fruit mature in March—April, about 1 month later than those of TDE4. Encore fruit always have a distinctive green or dark brown spot or blotch on the rind which is absent on TDE4 fruit. The average size of TDE4 fruit is larger than that of Encore. Encore fruit have an aspect ratio of 0.71 and much thinner rinds (2.0 mm) while those of TDE4 has an aspect ratio of 0.78 and rinds 3.5 mm thick. Encore fruit hold extremely well on the tree (4–6 months). The height of mature (35 year old) Encore trees is about 4.1 m, shorter than that of mature (27 years old) TDE4 trees.

Vigor of TDE4 trees has varied greatly across locations. At CVARS, where the trees grew rapidly, canopy volumes of 7-year-old trees averaged 23.0 $m^3$. In contrast, at the cooler Santa Paula and Ojai locations, 7-year-old trees averaged 4.3 and 5.6 $m^3$. Trees in the desert locations have never produced fruit, perhaps contributing to greater vegetative growth. Rootstock affected tree size at some locations. At Lindcove and Orange Cove, trees on Carrizo were the largest, followed by C35, and then Cleo and trifoliate which were similar. At Ojai, the largest trees were on C35, followed by Schaub rough lemon and Carrizo. At CVARS, trees on Carrizo, C35 and Cleo were similar in size. At Santa Paula, the single tree on Carrizo was smallest than that on C35. No evidence of rootstock-scion incompatibilities was evident.

TDE4 can be propagated on many available *citrus* rootstocks by budding. To reduce thorniness, budwood should be selected from thornless, upper canopy branches. Tree spacing in field plantings will depend on vigor of the rootstock. For Carrizo citrange rootstocks, a recommended tree density is about 150 trees per acre. Higher densities are possible, but will require more frequent pruning or hedging. Care of young trees should be similar to that used for other mandarins or oranges. Trees can be grown with pollinizer cultivars such as Minneola, Valencia orange, or unrelated mandarins (not Temple, Dancy, Encore of other TDE hybrids) that produce viable pollen. Optimal pruning practices have not yet been developed, but in many locations trees will perform well with relatively little pruning. Maturity dates will vary with location, probably depending on the number of heat units and soil conditions.

As with some other mandarin, sprays and gibberellic acid may increase fruit set when pollinizers and/or pollinators are inadequate.

TDE4 trees are winter hardy in USDA zones 9b to 11.

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence:PCR primer
      TAA3F

<400> SEQUENCE: 1

agagaagaaa catttgcgga gc                                              22


<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence:PCR primer
      TAA3R

<400> SEQUENCE: 2

gagatgggac ttggttcatc acg                                             23


<210> SEQ ID NO 3
<211> LENGTH: 22
<212> TYPE: DNA
```

-continued

```
<213> ORGANISM: Artificial Sequence
<220> FEATURE:
<223> OTHER INFORMATION: Description of Artificial Sequence:PCR primer
      CAC15 F

<400> SEQUENCE: 3

taaatctcca ctctgcaaaa gc                                              22


<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:PCR primer
      CAC15 R

<400> SEQUENCE: 4

gataggaagc gtcgtagacc c                                               21


<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:PCR primer
      TAA15 F

<400> SEQUENCE: 5

gaaagggtta cttgaccagg c                                               21


<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:PCR primer
      TAA15 R

<400> SEQUENCE: 6

cttcccagct gcacaagc                                                   18
```

What is claimed is:

1. A new and distinct variety of mandarin hybrid tree having substantially the characteristics described and illustrated herein.

* * * * *

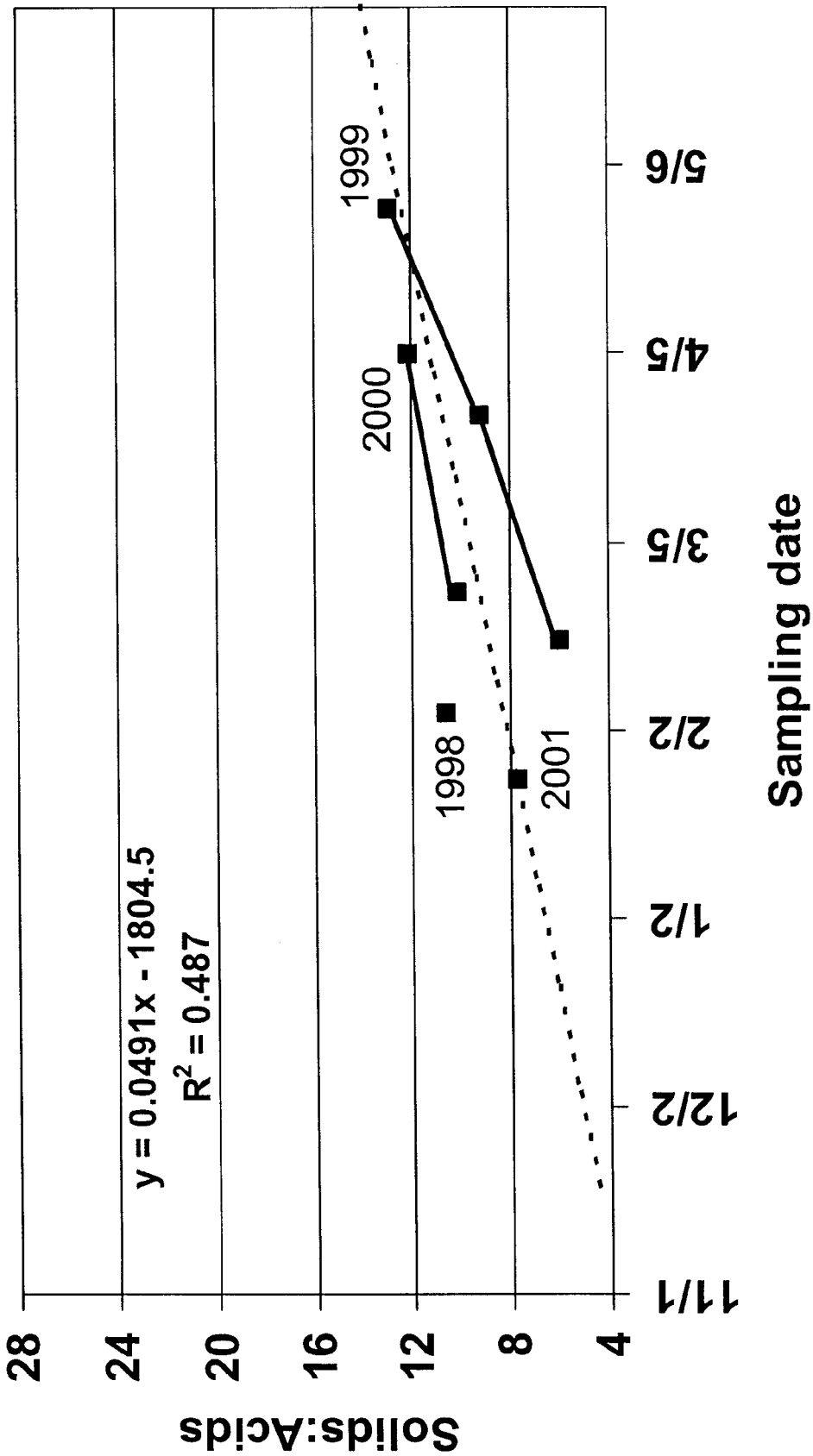
Figure 4. Solids:Acid of TDE4 at Santa Paula, CA

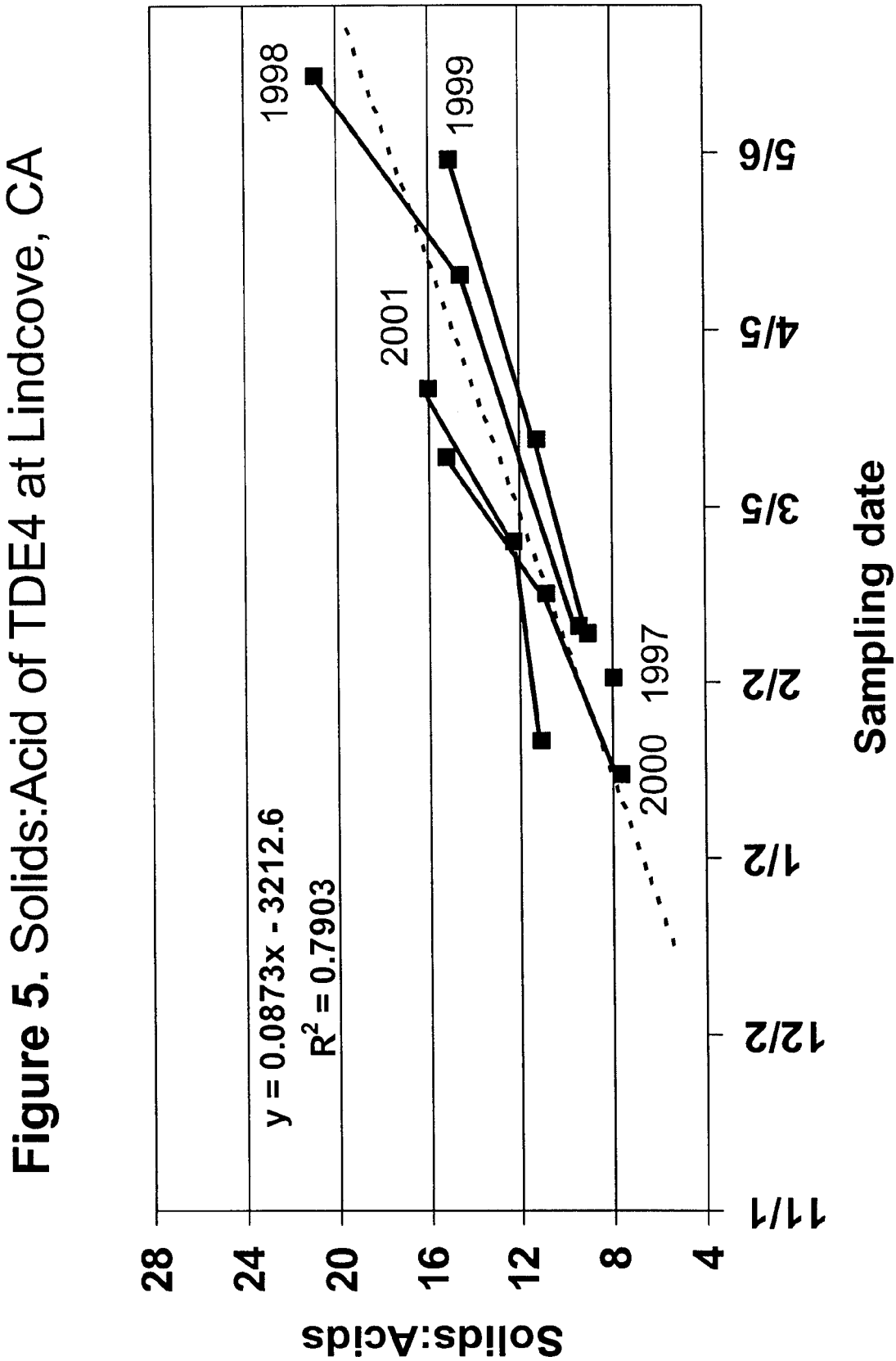
Figure 5. Solids:Acid of TDE4 at Lindcove, CA

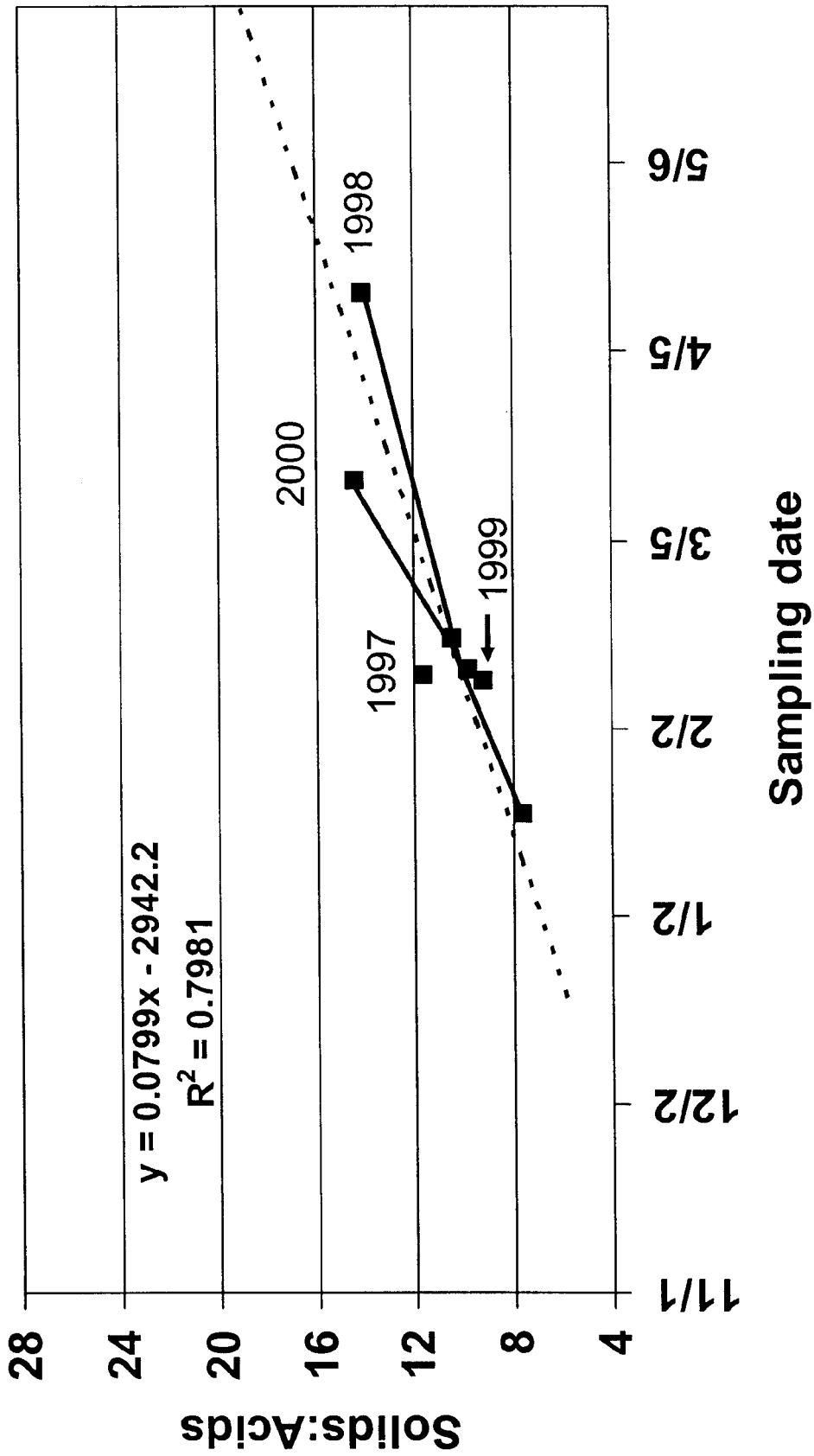
Figure 6. Solids:Acid of TDE4 at Orange Cove, CA

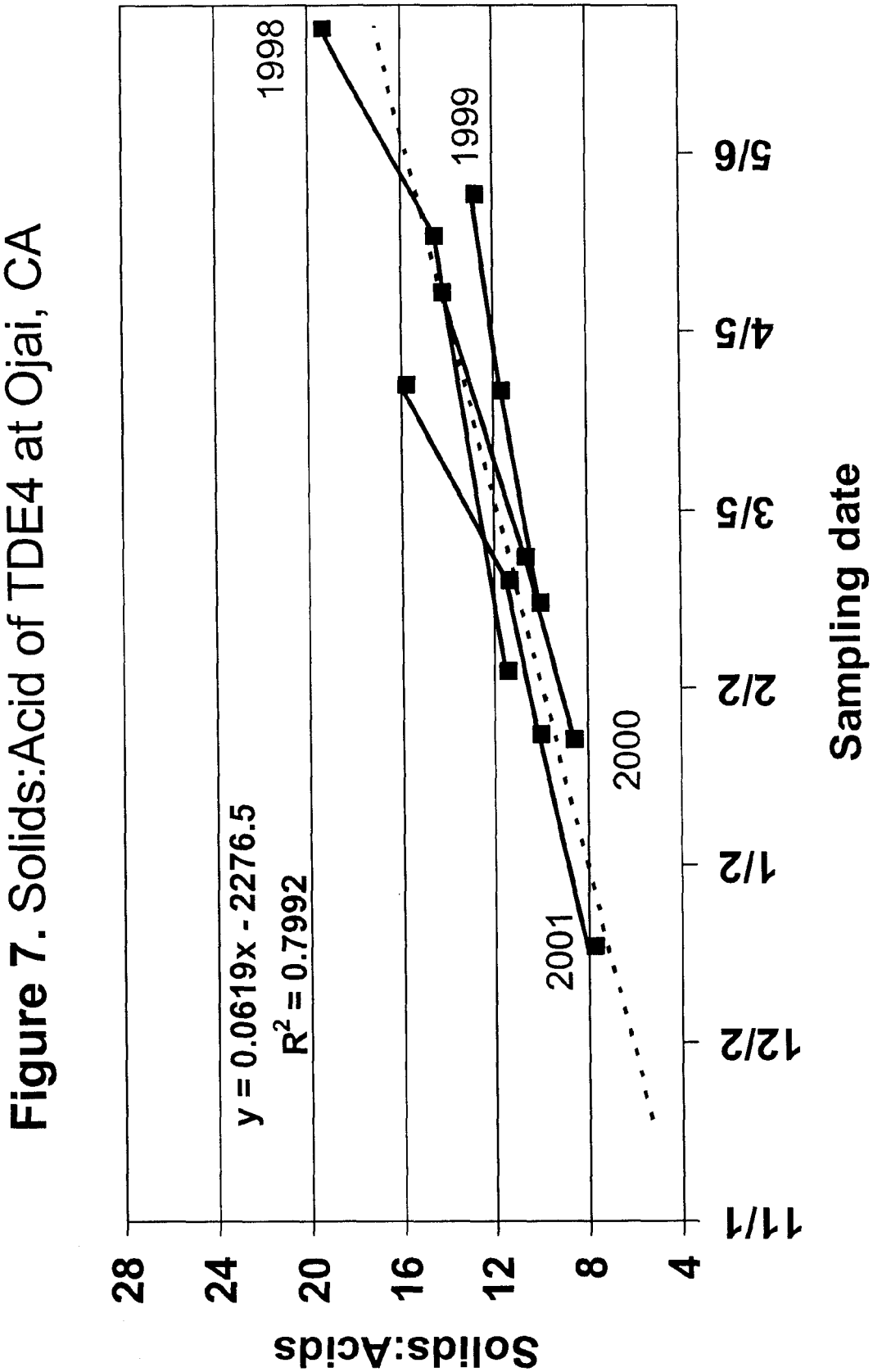
Figure 7. Solids:Acid of TDE4 at Ojai, CA
y = 0.0619x - 2276.5
R2 = 0.7992
1998
1999
2000
2001
Solids:Acids
28
24
20
16
12
8
4
11/1
12/2
1/2
2/2
3/5
4/5
5/6
Sampling date

UNITED STATES PATENT AND TRADEMARK OFFICE

CERTIFICATE OF CORRECTION

PATENT NO. : PP 16,289 P3
DATED : February 28, 2006
INVENTOR(S) : Mikeal L. Roose et al.

It is certified that error appears in the above-identified patent and that said Letters Patent is hereby corrected as shown below:

Title page,
Item [75], Inventors, change second inventor's name from "Timothy A. Williams" to -- Timothy E. Williams --.

Signed and Sealed this

Sixth Day of June, 2006

JON W. DUDAS
*Director of the United States Patent and Trademark Office*